(12) United States Patent
Wiedmann

(10) Patent No.: US 7,617,656 B2
(45) Date of Patent: Nov. 17, 2009

(54) METHOD AND APPARATUS FOR SELECTIVE FOLDING OR REDIRECTING

(75) Inventor: Peter Wiedmann, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 21 days.

(21) Appl. No.: 11/724,699

(22) Filed: Mar. 16, 2007

(65) Prior Publication Data

US 2008/0223537 A1 Sep. 18, 2008

(51) Int. Cl.
*B65B 63/04* (2006.01)

(52) U.S. Cl. .................. 53/429; 53/116; 53/53; 53/54; 493/12; 493/16; 493/23

(58) Field of Classification Search ............ 53/53, 53/54, 65, 429, 433, 116; 493/8, 12, 16, 493/405, 419, 424–427, 429, 23, 431, 436
See application file for complete search history.

(56) References Cited

U.S. PATENT DOCUMENTS

| | | | |
|---|---|---|---|
| 3,339,914 A * | 9/1967 | Grantham | 493/23 |
| 3,692,303 A * | 9/1972 | Grantham | 493/15 |
| 4,519,596 A | 5/1985 | Johnson et al. | |
| 4,650,173 A | 3/1987 | Johnson et al. | |
| 4,738,440 A | 4/1988 | Weir | |
| 5,980,439 A * | 11/1999 | Johnson et al. | 493/14 |
| 6,708,855 B2 | 3/2004 | Wilson et al. | |
| 6,915,929 B2 * | 7/2005 | Rauch et al. | 223/37 |
| 2001/0038709 A1 * | 11/2001 | Bett et al. | 382/141 |
| 2003/0062121 A1 | 4/2003 | Allan | |
| 2003/0110739 A1 * | 6/2003 | Saas | 53/460 |

FOREIGN PATENT DOCUMENTS

GB 1 253 503 A 11/1971

OTHER PUBLICATIONS

International Search Report PCT/IB2008/050978 dated Sep. 12, 2008.

\* cited by examiner

*Primary Examiner*—Thanh K Truong
(74) *Attorney, Agent, or Firm*—Charles R. Matson

(57) ABSTRACT

The present disclosure relates to a method for redirecting cut web products and/or rejecting cut web products. The method comprises advancing a plurality of cut web products along a first path and providing a redirecting or folding device for folding the plurality of cut web products and/or delivering the folded cut web products to a second path. Prior to reaching the folding device, the cut web products may be determined to be defective. The folding device can be accelerated, decelerated, or substantially stopped, such that a selected cut web product is not delivered to the second path, thereby rejecting the selected cut web product. The present disclosure additionally comprises an apparatus for redirecting and/or rejecting cut web products.

15 Claims, 5 Drawing Sheets

METHOD AND APPARATUS FOR SELECTIVE FOLDING OR REDIRECTING

FIELD OF THE INVENTION

The present disclosure relates to a method and apparatus for selective folding or redirecting of cut web products. More particularly, the present disclosure relates to a method and apparatus for high speed selective folding, redirecting, and/or rejecting of cut web products, such as diapers or catamenials.

BACKGROUND OF THE INVENTION

In some instances, there may be a desire to redirect cut web products on a high speed production line to a different production stream. In other cases, some cut products manufactured on a high speed production line may contain defects. Several mechanisms exist for rejecting defective cut web products, such as by diverting the defective cut web products from the stream of cut web products that are of satisfactory condition or good quality. One method that has been used to reject cut web products includes forcing the defective cut web products out of the stream of satisfactory products by using pneumatic air blasts, which divert the defective cut web products to a path that differs from that for the stream of satisfactory products. In such a method, the defective cut web products are detected, and a pneumatic air blast forces the defective cut web products out of the stream of quality products and into a reject gap provided in the conveyor system or production line. Typically, the reject gap will be provided prior to subjecting the cut web products to further processing, such as folding. Methods of rejecting cut web products using pneumatic air blasts involve several disadvantages. Devices creating pneumatic air blasts require space. Similarly, extra space along the conveyor system is required to include a reject gap. A reject gap further involves system reliability issues related to having a gap in the conveyor system, such as jamming. Additionally, pneumatic air blasts create excessive dust and noise. Furthermore, pneumatic air blasts are not entirely accurate and can divert more than solely the defective cut web product from the stream of satisfactory products. Also, the equipment to create, convey, regulate, and control the air blast is expensive to install and operate.

A similar method of rejecting cut web products includes using a vacuum to remove the defective cut web products from the stream of quality products. The use of a vacuum, rather than pneumatic air blasts, involves similar disadvantages, such as requiring large amounts of space for the vacuum device, providing extra space along the conveyor system for the reject gap, creating excessive noise and dust, etc. Also, the additional vacuum equipment and vacuum creation, control, and transportation is expensive.

Another method of rejecting cut web products includes mechanically activated switches, or flippers, that divert the defective cut web products to an alternative pathway, similar to the manner railway switches can divert trains to a different track. The mechanical switches are commonly activated via a pneumatic or hydraulic cylinder or via an electric motor. A typical configuration includes mechanical switches that pop up from the conveyor system and divert the defective cut web products below the switch towards an alternate pathway. Rejection of defective cut web products typically takes place before the cut web products are subjected to further processing, such as folding. As such, more space is required to create room for the mechanically activated switches and the alternate pathway. Thus, space consumption is a disadvantage to the mechanical switch method. Furthermore, the additional mechanical switch equipment is expensive.

A method and apparatus for high speed selective folding, redirecting, and/or rejecting of cut web products that is compact may be desirable. Further, a method and apparatus that is accurate in removing only the selected cut web products from the stream of quality products may also be desirable. Further, a method and apparatus that creates less noise and dust may be desirable. A method and system that does not need a reject gap in the conveyor system also may be desirable. Additionally, a system that uses existing equipment and control mechanisms to reject products rather than adding equipment and ancillary devices to perform this task may be desirable.

SUMMARY OF THE INVENTION

The present disclosure, in an embodiment, is a method for rejecting defective cut web products. A plurality of cut web products may advance along a first path. A folding device may be provided for folding the cut web products and delivering the folded cut web products to a second path. Some of the cut web products may be determined to be defective. As such, the folding device may be slowed down, substantially slowed down, or substantially stopped, such that the defective cut web product is not delivered to the second path.

The present disclosure, in another embodiment, is an apparatus for selectively folding cut web products. The apparatus may include first and second pathways for conveying cut web products, and a folding device along the first pathway for folding cut web products and delivering them to the second pathway. The folding device may include a tucker and a driver. The driver may contain programming to stop and restart the tucker and generally control the tucker.

While multiple embodiments are disclosed, still other embodiments of the present disclosure will become apparent to those skilled in the art from the following detailed description, which shows and describes illustrative embodiments of the invention. As will be realized, the invention is capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the present disclosure, it is believed that the invention will be better understood from the following description taken in conjunction with the accompanying figures, in which:

DETAILED DESCRIPTION OF THE INVENTION

The present disclosure relates to a novel and advantageous method and apparatus for selectively folding, redirecting, and/or rejecting a cut web product. The method and apparatus of the present disclosure may be used with any suitable cut web product. Examples of cut web products that may be used with the present disclosure include, but are not limited to, diapers, napkins, wet wipes, feminine care products, paper products, packaged products, etc. In some embodiments of the selective folding apparatus of the present disclosure, it may be desirable to redirect or reject a particular cut web product, for example when a particular cut web product is determined to contain a defect. A cut web product alternatively may be redirected or rejected for any number of reasons, including for any variety of reasons that the cut web product is unsatisfactory in any characteristic. In one embodiment, where it is desirable to redirect or reject a particular cut web product, it may further be desirable to allow the cut web product to pass or bypass a folding portion of the selective folding apparatus.

Figure 1:
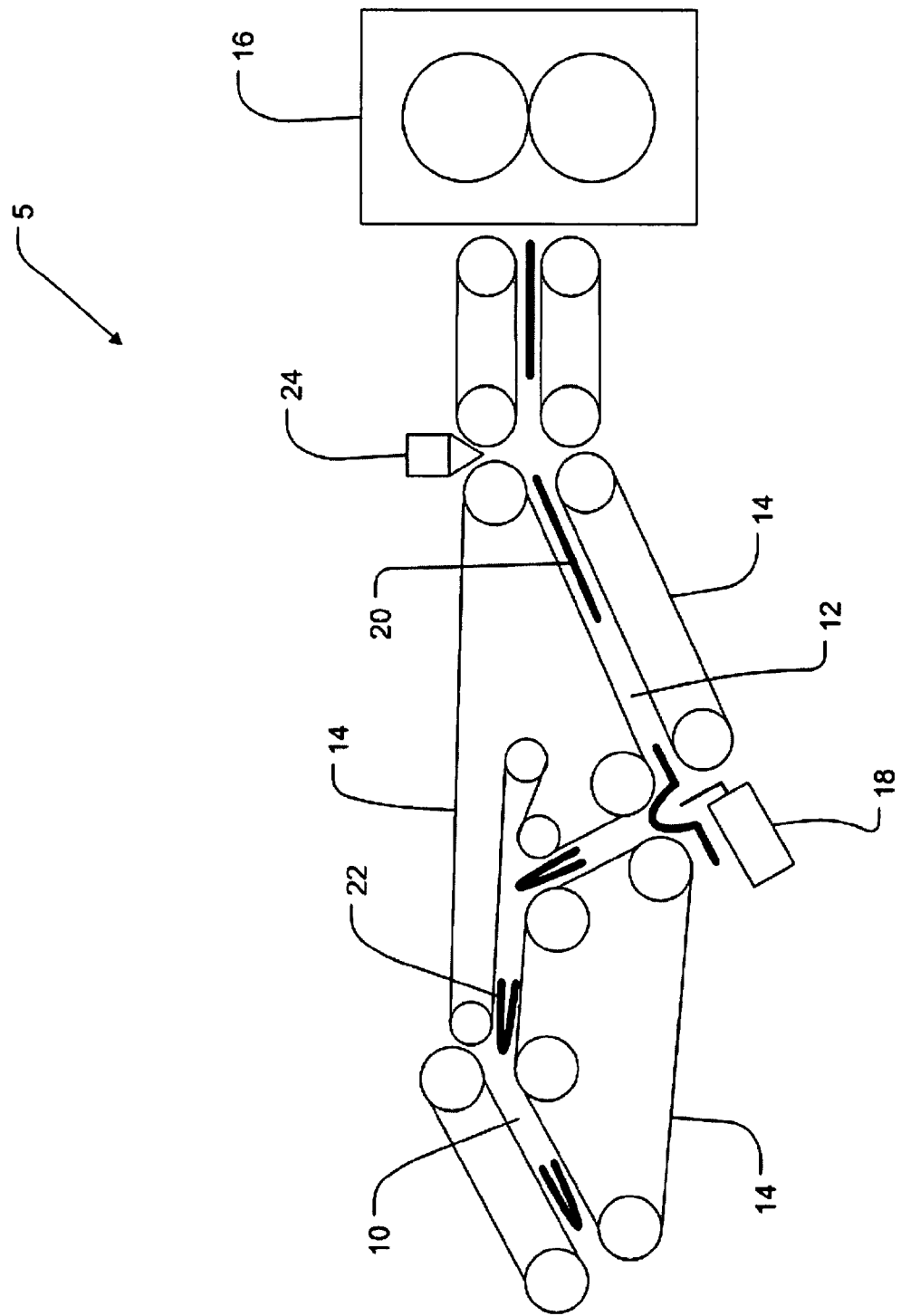
FIG. 1 is a side view of a selective folding apparatus in accordance with an embodiment of the present disclosure.

FIG. 1 illustrates an embodiment of a selective folding apparatus generally designated as numeral 5. Selective folding apparatus 5 may include a first pathway 12 for cut web products 20, a second pathway 10 for redirected or folded cut web products 22, a conveyor system 14, and a redirecting or folding mechanism 18 for folding cut web products 20 and delivering folded cut web products 22 to second pathway 10. In some embodiments, selective folding apparatus 5 may further include a defect sensor 24, for detecting cut web products 20 that contain at least one defect or otherwise do not meet satisfactory conditions.

In a further embodiment, selective folding apparatus 5 may include a cutting device 16 for cutting a continuous length of web material into cut web products 20 prior to delivering cut web products 20 to first pathway 12. In an embodiment shown in FIG. 1, the cutting device 16 is shown adjacent to first pathway 12. In other embodiments, cutting device 16 need not be adjacent first pathway 12, and selective folding apparatus 5 may comprise one or more intermediary paths or subject cut web products 20 to further processes prior to entering first pathway 12. In yet other embodiments, selective folding apparatus 5 need not include cutting device 16 nor be attached to any other intermediary paths or further processing devices and may comprise a standalone apparatus.

As illustrated in FIG. 1, in an embodiment, cut web products 20 are delivered, manually or mechanically, to first pathway 12. Cut web products 20 travel along first pathway 12 by means of conveyor system 14. In an embodiment, conveyor system 14 comprises a belt and roller system. In other embodiments, conveyor system 14 may comprise any other suitable mechanism, including but not limited to, a conveyor or transport drum, for causing cut web products 20 to travel along first pathway 12.

Cut web products 20 travel along first pathway 12 toward folding mechanism 18. In an embodiment, folding mechanism 18 may selectively cause cut web products 20 to be folded and may further cause the folded cut web products 22 to be delivered to second pathway 10. In some embodiments, folded cut web products 22 may travel along second pathway 10 by means of conveyor system 14 toward an exit of selective folding apparatus 5. In further embodiments, folded cut web products 22 may travel along other paths or be subjected to further processing, such as testing, stacking, packaging, etc. For example, in an embodiment, folded cut web products 22 may travel along second pathway 10 toward a second folding mechanism, whereby folded cut web products 22 are folded, selectively folded, or redirected a second time. In a further example, folding mechanism 18 may fold, or selectively fold, cut web products 20 across a first fold, wherein a first portion of cut web products 20 are folded over a second portion of cut web products 20. The partially folded cut web products may then be delivered to a second folding mechanism, whereby the partially folded cut web products may be folded, or selectively folded, a second time, such that a third portion of cut web products 20 is folded over the first/second folded portions of cut web products 20, such as wherein a tri-folded cut web product is desired. In alternative embodiments, cut web products 20 may pass by, and be selectively subjected to, any number of folding mechanisms, such as three, four, or more folding mechanisms. In some embodiments, multiple folding mechanisms may be desired for any number of reasons, including but not limited to, directing cut web products 20 to alternate pathways, creating multiple folds in cut web products 20, rejecting cut web products 20 based on specific characteristics, etc.

Figure 2:
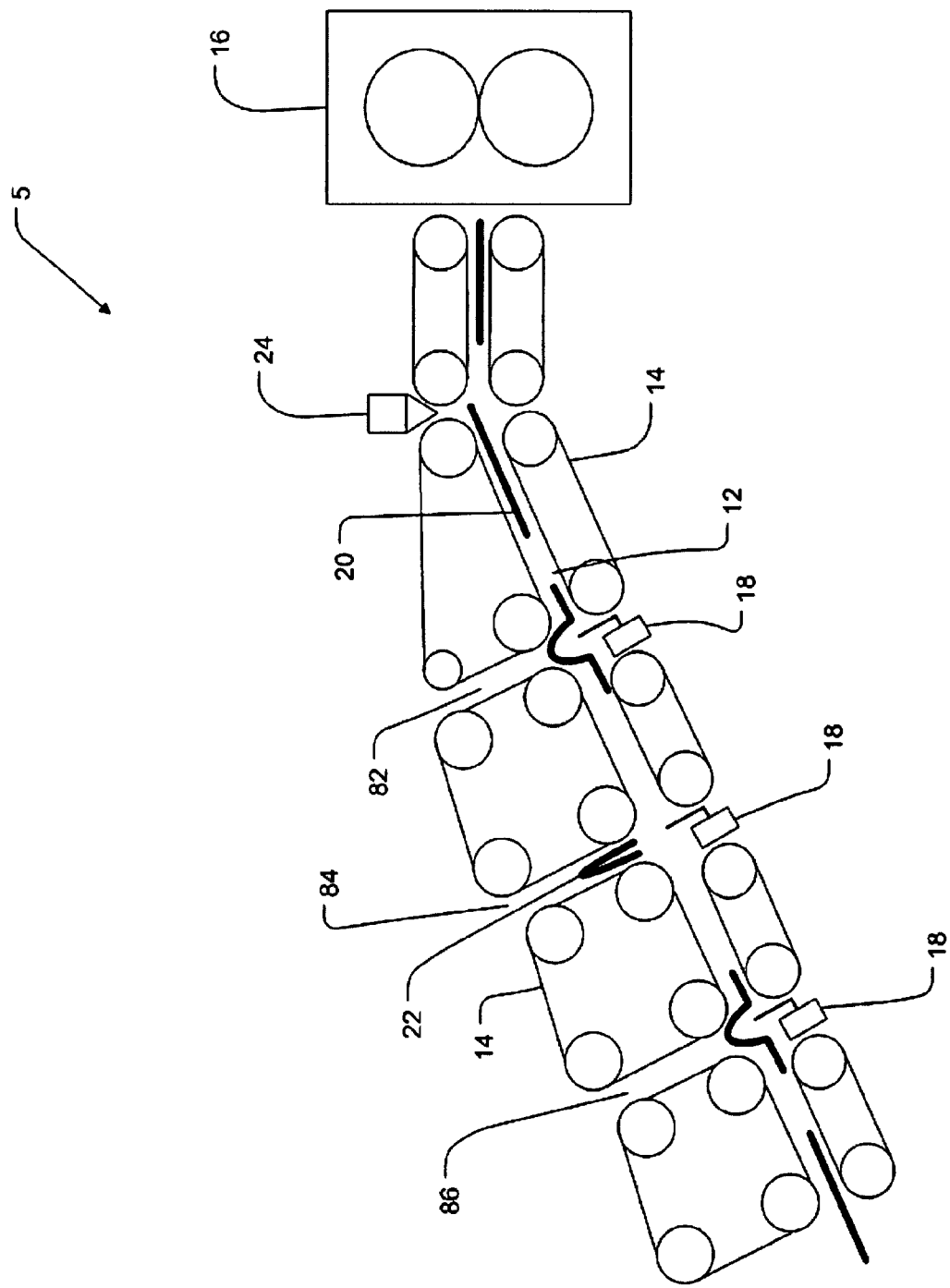
FIG. 2 is a side view of a selective folding apparatus in accordance with another embodiment of the present disclosure.

In an embodiment of selective folding apparatus 5, shown in FIG. 2, one or more second pathways 82, 84, 86 may be provided for which cut web products 20 may be redirected from first pathway 12. In an embodiment, a single pathway may be provided, while in other embodiments two or more pathways may be provided. In a further embodiment, any of cut web products 20 may be redirected to any of multiple second pathways 82, 84, 86. Cut web products 20 may be redirected to any particular pathway for any number of reasons and is not limited to merely redirecting defective cut web products or folded cut web products 22. For example, in an embodiment, multiple second pathways 82, 84, 86 may provide separate pathways for folding cut web products 20 using alternative methods of folding, such as, but not limited to, bi-folding, tri-folding, quad-folding, wrapping, rolling, or hand folding, or any combination thereof, including providing one or more second pathways 82, 84, 86 for any method of folding. In another embodiment, a selected number of cut web products 20 may be redirected to one or more second pathways 82, 84, 86 for reasons relating to, but not limited to, the speed of conveyor system 14, the relative line speed of first pathway 12 compared with the speed of an apparatus used for folding, stacking, packaging, etc. on second pathways 82, 84, 86, or any other characteristic of selective folding apparatus 5 relating to the effects of production line speeds on the resulting end product. In yet another embodiment, cut web products 20 traveling along first pathway 12 may be selected for redirection to one of the multiple second pathways 82, 84, 86, such that half of cut web products 20 are redirected to a particular second pathway, a third of cut web products 20 are redirected to a particular second pathway, a fourth of cut web products 20 are delivered to a particular second pathway, or any other suitable fraction of cut web products 20 traveling along first pathway 12 may be redirected to a particular second pathway. As such, the product stream of cut web products 20 may be divided among more than one second pathway for further processing. Further processing in any of the multiple second pathways 82, 84, 86 may include, but is not limited to, folding, testing, stacking, packaging, etc. Furthermore, the processing in any particular second pathway 82, 84, 86 may differ from the processing in any of the other multiple second pathways 82, 84, 86.

Figure 3A:
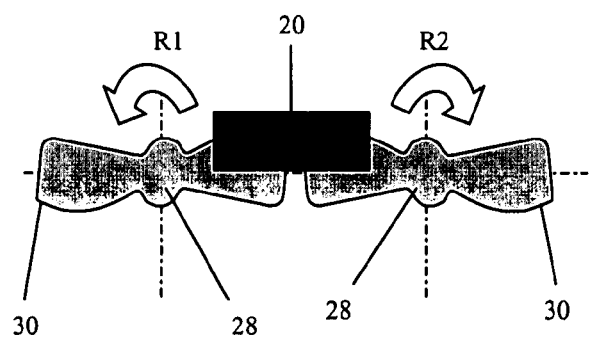
FIG. 3A is a front view of a folding mechanism of a selective folding apparatus in accordance with another embodiment of the present disclosure.

In an embodiment of selective folding apparatus 5, shown in FIG. 3A, folding mechanism 18 may include dual propeller-style tuckers 28, which rotate in opposite directions, indicated by rotational arrows R1 and R2. In a further embodiment, folding mechanism 18 comprises dual propeller-style tuckers 28, each propeller-style tucker having two blades 30 each. In other embodiments, a fewer or greater number of blades 30 may be provided on each propeller-style tucker 28. For example, propeller-style tucker 28 may comprise a single blade 30 or may comprise three or more blades 30. In yet other embodiments, it is recognized that a single propeller-style tucker 28 may be provided instead of dual propeller-style tuckers 28. It is recognized further that any suitable number of propeller-style tuckers 28, each with any suitable number of blades 30, may be provided. The blades may be provided in any desired shape or configuration.

Figure 3B:
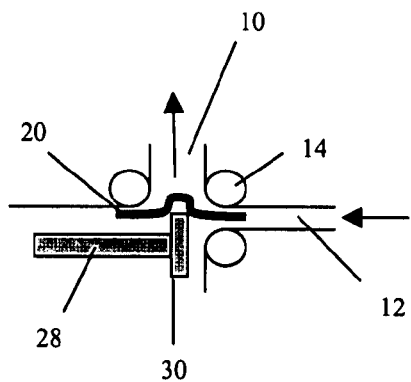
FIG. 3B is a side view of a folding mechanism of a selective folding apparatus in accordance with an embodiment of a folding mechanism of FIG. 3A.

As can be seen in FIG. 3B, propeller-style tuckers 28 may be phased such that blades 30 engage cut web products 20 as the cut web products 20 travel along first pathway 12 and pass by folding mechanism 18. Blades 30 may engage cut web products 20 for folding at any position. For example, in an embodiment, blades 30 may engage cut web products 20 at a substantially center position, thereby folding cut web products 20 substantially in half. However, it is recognized that blades 30 may engage cut web products 20 in a position other than substantially at the center of cut web products 20, as may be done when cut web products 20 will be folded more than a single time. Dual propeller style tuckers 28 may further direct folded cut web products 22 to second pathway 10. In an embodiment, folding mechanism 18 may direct cut web products 20 to second pathway 10 without folding cut web products 20. For example, in an embodiment, dual propeller-style tuckers 28 may direct cut web products 20 to second pathway 10 without folding cut web products 20 by redirecting a leading tip, or edge, of cut web products 20.

Figure 4A:
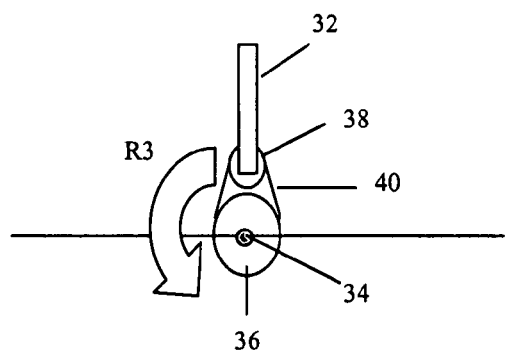
FIG. 4A is a side view of a folding mechanism of a selective folding apparatus in accordance with yet another embodiment of the present disclosure.

FIG. 4A illustrates a further embodiment of folding mechanism 18. Folding mechanism 18 may include tucker blade 32, shaft 34, fixed gear 36, rotating gear 38, and drive belt 40. Rotating gear 38 may orbit fixed gear 36, as shown by rotational arrow R3. In a further embodiment, fixed gear 36 and drive belt 40 may cause rotating gear 38 to rotate around its central axis. One end of tucker blade 32 may be fixed at substantially near the central axis of rotating gear 38, thereby causing tucker blade 32 to rotate with rotating gear 38. Other suitable means may be used for obtaining substantially the same effect and rotation of tucker blade 32, including, for example, replacing drive belt 40 with at least one gear or gearbox. It is further recognized that more than one rotating gear 38 and tucker blade 32 may be provided to orbit fixed gear 36.

Figure 4B:
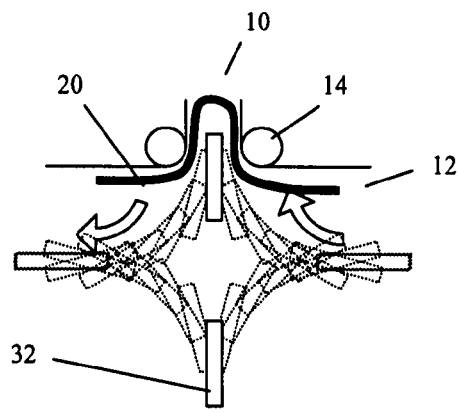
FIG. 4B is a side view of the path followed by a folding mechanism of a selective folding apparatus in accordance with an embodiment of a folding mechanism of FIG. 4A.

FIG. 4B illustrates a path that may be followed by tucker blade 32 in an embodiment of folding mechanism 18 illustrated in FIG. 4A. The dashed-line tucker blades represent positions that tucker blade 32 may be located at some time throughout the orbit and rotation of rotating gear 38. For ease of illustration, embodiments of shaft 34, fixed gear 36, rotating gear 38, and drive belt 40 have been removed from FIG. 4B.

As can be seen in FIG. 4B, folding mechanism 18 may be phased such that tucker blade 32 engages cut web products 20 as the cut web products 20 travel along first pathway 12 and pass by folding mechanism 18. Tucker blade 32 may engage cut web products 20 for folding at any position. For example, in an embodiment, tucker blade 32 may engage cut web products 20 at a substantially center position, thereby folding cut web products 20 substantially in half. However, as previously stated, it is recognized that tucker blade 32 may engage folding cut web products 20 in a position other than substantially at the center of cut web products 20, as may be done when cut web products 20 will be folded more than a single time. Tucker blade 32 may further direct folded cut web products 22 to second pathway 10. As previously described, in an embodiment, folding mechanism 18 may direct cut web products 20 to second pathway 10 without folding cut web products 20. For example, in an embodiment, tucker blade 32 may direct cut web products 20 to second pathway 10 without folding cut web products 20 by redirecting a leading tip, or edge, of cut web products 20.

Figure 5A:
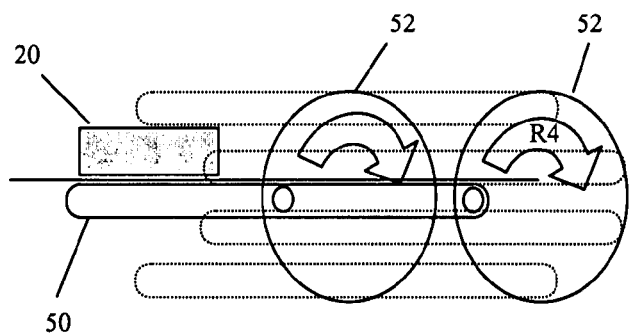
FIG. 5A is a front view of a folding mechanism of a selective folding apparatus in accordance with a further embodiment of the present disclosure.

Yet another embodiment of folding mechanism 18 can be seen in FIG. 5A. Folding mechanism may include tucker arm 50 and rotating arm 52. Tucker arm 50 may be attached at one end to rotating arm 52. Rotating arm 52 may rotate in place around a central axis of rotating arm 52, such as is illustrated by rotational arrow R4. In some embodiments, folding mechanism 18 may include more than one rotating arm 52, as shown in FIG. 5A. In further embodiments, rotating arm 52 may be a rotating bar, rotating plate, or rotating planetary gear system, or any other suitable structure or configuration. It is recognized that any means for rotating may be used for, or in place of, rotating arm 52. As rotating arm 52 rotates, tucker arm 50 may follow the path shown by the dashed-line tucker arms in FIG. 5A. The dashed-line tucker arms represent positions that tucker arm 50 may be located at some time throughout the orbit and rotation of rotating arm 52. As can be seen in FIG. 5A, as tucker arm 50 rotates with rotating arm 52, it may maintain a configuration wherein at any position during rotation, tucker arm 50 may be substantially parallel to any other position during rotation of tucker arm 50.

Figure 5B:
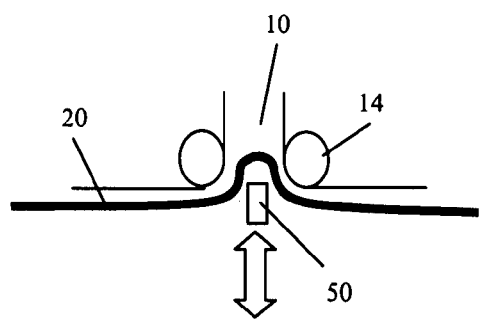
FIG. 5B is a side view of a folding mechanism of a selective folding apparatus in accordance with an embodiment of a folding mechanism of FIG. 5A.

As can be seen in FIG. 5B, folding mechanism 18 may be phased such that tucker arm 50 engages cut web products 20 as the cut web products 20 travel along first pathway 12 and pass by folding mechanism 18. Tucker arm 50 may engage cut web products 20 for folding at any position. For example, in an embodiment, tucker arm 50 may engage cut web products 20 at a substantially center position, thereby folding cut web products 20 substantially in half. However, as previously stated, it is recognized that tucker arm 50 may engage folding cut web products 20 in a position other than substantially at the center of cut web products 20, as may be done when cut web products 20 will be folded more than a single time. Tucker arm 50 may further direct folded cut web products 22 to second pathway 10. As previously described, in an embodiment, folding mechanism 18 may direct cut web products 20 to second pathway 10 without folding cut web products 20. For example, in an embodiment, tucker arm 50 may direct cut web products 20 to second pathway 10 without folding cut web products 20 by redirecting a leading tip, or edge, of cut web products 20.

Other suitable forms of folding mechanism 18 also may be appropriate for use with some embodiments of selective folding apparatus 5 of the present disclosure. It is further recognized that the terms tucker, tucker blade, or tucker arm may refer to any suitable mechanism for engaging the cut web products 20 and causing the cut web products 20 to be redirected and/or folded about an axis—typically, though not exclusively, an imaginary line—that defines two or more generally symmetrical or asymmetrical portions of the cut web product 20. Furthermore, tucker blades 30 and 32 and tucker arm 50 may be manufactured from any suitable materials such as, but not limited to, metal, metallic alloys, plastics, etc., or combinations thereof.

Figure 6:
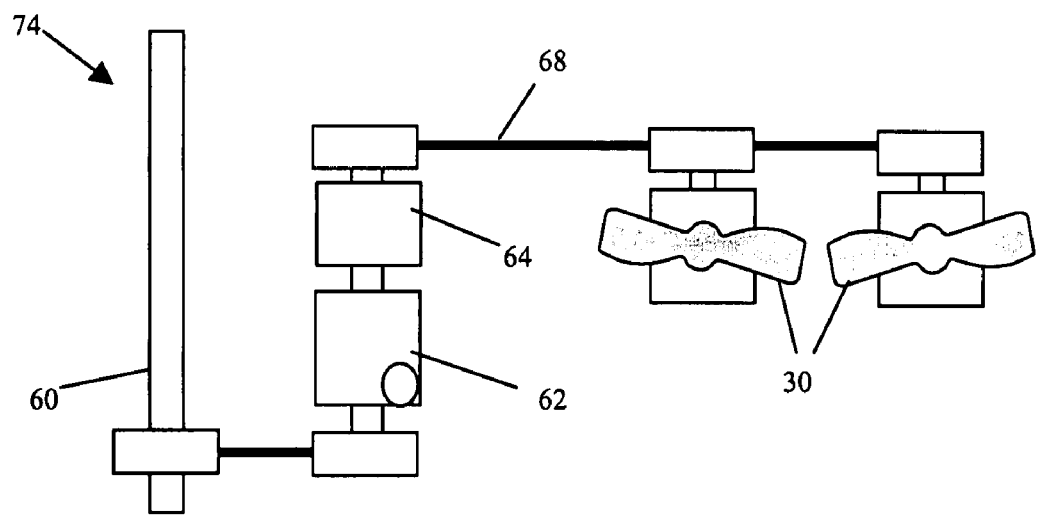
FIG. 6 is a front view of a drive mechanism of a folding mechanism of a selective folding apparatus in accordance with another embodiment of the present disclosure.

Folding mechanism 18 may comprise any drive mechanism 74 for operating a tucker blade. In an embodiment of folding mechanism 18, illustrated in FIG. 6, drive mechanism 74 may be a line shaft drive mechanism comprising main shaft 60, phasing gear box 62, disengagement clutch 64, and linking belt 68. Not all components of the line shaft drive mechanism shown in FIG. 6 are required, and some components may be eliminated from the line shaft drive mechanism without departing from the scope of the present disclosure, while others may be added or substituted. In an embodiment, main shaft 60 may directly drive the folding mechanism 18. In a further embodiment, main shaft 60 may indirectly drive the folding mechanism 18. For example, in an embodiment, the main shaft 60 may be linked to phasing gear box 62, which may phase the driving rotation of main shaft 60 to align the engagement of folding mechanism 18 with passing cut web products 20. A line shaft drive mechanism may further include disengagement clutch 64. Disengagement clutch 64 may cause folding mechanism 18 to slow down, stop, and/or restart during operation of selective folding apparatus 5. That is, at any suitable moment, disengagement clutch 64 may cause drive mechanism 74 to slow down or stop, which may further prevent folding mechanism 18 from engaging cut web product 20, folding cut web product 20, or delivering cut web product 20 to second pathway 10. In other embodiments, disengagement clutch 64 may be replaced by other suitable mechanisms for slowing or stopping folding mechanism 18 from engaging cut web product 20, folding cut web product 20, or delivering cut web product 20 to second pathway 10. Linking belt 68 may link main shaft 60, phasing gear box 62, or disengagement clutch 64 with tucker blades 30 or 32 or tucker arm 50. In an embodiment, linking belt 68 may be a belt or chain. In alternative embodiments, linking belt 68 may be any suitable means for connecting main shaft 60, phasing gear box 62, or disengagement clutch 64 with tucker blades 30 or 32 or tucker arm 50, such that drive mechanism 74 is linked to tucker blades 30 or 32 or tucker arm 50, such as via gears or gearboxes.

Figure 7:
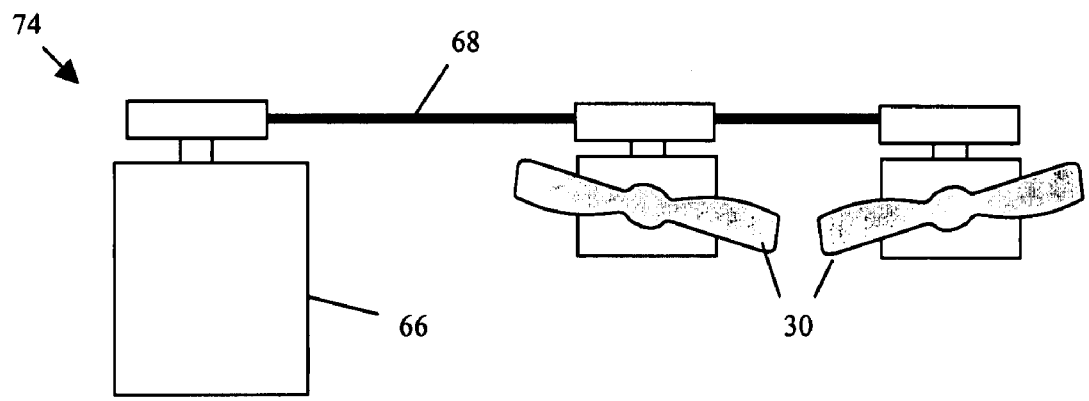
FIG. 7 is a front view of a drive mechanism of a folding mechanism of a selective folding apparatus in accordance with yet another embodiment of the present disclosure.

In another embodiment, illustrated in FIG. 7, drive mechanism 74 may include motor 66 and linking belt 68. Motor 66, in a further embodiment, may be a servo motor for controlling the position of tucker blades 30 or 32 or tucker arm 50 of folding mechanism 18. A servo motor may be used to alter the speed of folding mechanism 18 quickly, including accelerating, decelerating, stopping, and restarting folding mechanism 18 in a very short period of time. For example, a servo motor may be used to accelerate, decelerate, stop, and restart folding mechanism 18, including in a relatively short period of time, such as seconds or fractions of a second, such as milliseconds. In other embodiments a servo motor may be used to accelerate, decelerate, stop, and restart folding mechanism 18 in any interval of time. Linking belt 68 may link motor 66 with tucker blades 30 or 32 or tucker arm 50. As previously stated, linking belt 68 may be a belt or chain. In alternative embodiments, linking belt 68 may be any suitable means for linking motor 66 with tucker blades 30 or 32 or tucker arm 50, such that drive mechanism 74 is linked to tucker blades 30 or 32 or tucker arm 50, such as via gears or gearboxes. Drive mechanism 74, illustrated in FIG. 7, may provide less driven inertia and lower momentum forces during slowing or stopping of folding mechanism 18 and may allow faster conveyor speeds and higher precision of folding mechanism 18 than the mechanism illustrated in FIG. 6.

Figure 8:
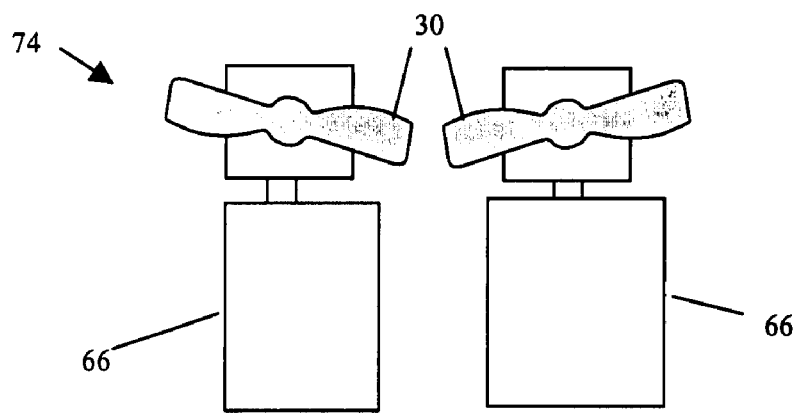
FIG. 8 is a front view of a drive mechanism of a folding mechanism of a selective folding apparatus in accordance with a further embodiment of the present disclosure.

In yet a further embodiment, shown in FIG. 8, linking belt 68 may be eliminated from drive mechanism 74. Motor 66, such as a servo motor, may be linked directly to tucker blades 30 or 32 or tucker arm 50, such that the motor 66 directly controls tucker blades 30 or 32 or tucker arm 50. Drive mechanism 74, illustrated in FIG. 8, may provide even less driven inertia and lower momentum forces during slowing or stopping of folding mechanism 18 and may allow even faster conveyor speeds and higher precision of folding mechanism 18 than the mechanisms in FIG. 6 or 7.

Although folding mechanism 18 illustrated in FIGS. 6-8 includes dual propeller-style tuckers 28, it is recognized that any tucker blade, or any other suitable structure, may be used in accordance with folding mechanism 18 of the present disclosure. For example, folding mechanism 18 may comprise any tucker blade system described above in combination with any drive mechanism 74 described above. Alternatively, folding mechanism 18 may comprise any suitable tucker blade system in combination with any suitable drive mechanism.

In an embodiment of selective folding apparatus 5, cut web products 20 are delivered, manually or mechanically, to first pathway 12. Cut web products 20 travel along first pathway 12 by means of conveyor system 14 toward folding mechanism 18. In an embodiment, folding mechanism 18 may selectively cause cut web products 20 to be folded and may further cause the folded cut web products 22 to be delivered to second pathway 10. That is, folding mechanism 18, in an embodiment, may cause some cut web products 20 to be folded and delivered to second pathway 10 while folding mechanism 18 allows other cut web products 20 to pass by without causing the cut web products 20 to be folded or delivered to second pathway 10.

Folding mechanism 18, in an embodiment, may allow some cut web products 20 to pass without being folded and delivered to second pathway 10 by slowing down, such that folding mechanism 18 does not engage the cut web products 20 that have been selected to bypass folding mechanism 18. In a further embodiment, folding mechanism 18 may allow some cut web products 20 to pass without being folded and delivered to second pathway 10 by stopping, or pausing, the tucker blades or tucker arm in mid-operation, such that folding mechanism 18 is stopped in a position that avoids engagement with cut web products 20 that have been selected to bypass folding mechanism 18. After cut web product 20 bypasses folding mechanism 18, folding mechanism 18 may be accelerated to operating speed or to another suitable speed. In an embodiment, folding mechanism 18 may be accelerated to operating speed by the time the next consecutive cut web product 20, which immediately follows the cut web product 20 that was selected to bypass folding mechanism 18, reaches folding mechanism 18. In such an embodiment, folding mechanism 18 need not be disengaged, physically and/or mechanically, from an engaging position to a non-engaging position, thereby reducing the need for space and/or moving parts.

In a further embodiment, folding mechanism 18 may be accelerated, or substantially accelerated, such that the tucker blades or tucker arm may be allowed to pass through first pathway 12 between consecutive cut web products 20, such that the tucker blades or tucker arm do not contact cut web products 20 that have been selected to bypass folding mechanism 18. Subsequent to acceleration, folding mechanism 18 may reduce its speed to substantially the same speed as during prior operation, or another suitable speed, such that the tucker blades or tucker arm may continue to pass through first pathway 12 between consecutive cut web products 20, thereby allowing consecutive cut web products 20 to bypass folding mechanism 18. That is, folding mechanism 18 may be accelerated or substantially accelerated, and then slowed or substantially slowed, such that the tucker blades or tucker arm are in a position that does not redirect cut web products 20 to second pathway 10. That is, folding mechanism 18 may be accelerated or substantially accelerated, and then slowed or substantially slowed, such that the tucker blades or tucker arm are out of phase with cut web products 20 traveling along first pathway 12. In an embodiment, folding mechanism 18 may be accelerated or substantially accelerated, and then slowed or substantially slowed, such that a single cut web product 20 is allowed to bypass folding mechanism 18, and then folding mechanism 18 may be phased, by acceleration or deceleration, back in accordance with cut web products 20 traveling along first pathway 12, such that cut web products 20 are once again folded and delivered to second pathway 10. In other embodiments, more than a single consecutive cut web product 20 may be allowed to bypass folding mechanism 18 before folding mechanism 18 is phased back in accordance with cut web products 20.

In a further embodiment, folding mechanism 18 may be decelerated, or substantially decelerated, such that the tucker blades or tucker arm may be allowed to pass through first pathway 12 between consecutive cut web products 20, such that the tucker blades or tucker arm do not contact cut web products 20 that have been selected to bypass folding mechanism 18. Subsequent a deceleration, folding mechanism 18 may increase its speed to substantially the same speed as during prior operation, or another suitable speed, such that the tucker blades or tucker arm may continue to pass through first pathway 12 between consecutive cut web products 20, thereby allowing consecutive cut web products 20 to bypass folding mechanism 18. That is, folding mechanism 18 may be decelerated or substantially decelerated, and then accelerated or substantially accelerated, such that the tucker blades or tucker arm are in a position that does not redirect cut web products 20 to second pathway 10. That is, folding mechanism 18 may be decelerated or substantially decelerated, and then accelerated or substantially accelerated, such that the tucker blades or tucker arm are out of phase with cut web products 20 traveling along first pathway 12. In an embodiment, folding mechanism 18 may be decelerated or substantially decelerated, and then accelerated or substantially accelerated, such that a single cut web product 20 is allowed to bypass folding mechanism 18, and then folding mechanism 18 may be phased, by acceleration or deceleration, back in accordance with cut web products 20 traveling along first pathway 12, such that cut web products 20 are once again folded and delivered to second pathway 10. In other embodiments, more than a single consecutive cut web product 20 may be allowed to bypass folding mechanism 18 before folding mechanism 18 is phased back in accordance with cut web products 20.

In an embodiment, cut web products 20 are selected to bypass folding mechanism 18 without being folded or delivered to second pathway 10 for any number of reasons, including but not limited to, defectiveness, testing purposes, etc., allowing cut web products 20 to pass to a different pathway other than second pathway 10. That is, cut web products 20 may be rejected, diverted, or sorted for any reason, including that cut web products 20 may be unsatisfactory in any characteristic or otherwise.

In some embodiments, selective folding apparatus 5 may further include a defect sensor 24 for detecting cut web products 20 that contain at least one defect or otherwise do not meet satisfactory conditions. In an embodiment, defect sensor 24 may be located prior to folding mechanism 18, such that defective cut web products are detected prior to reaching folding mechanism 18. In such an embodiment, defect sensor 24 may be located at any position prior to folding mechanism 18. Defect sensor 24 need not be located near folding mechanism 18. Additionally, defect sensor 24 need not be located near cutting device 16, as illustrated in the figures. In some embodiments, folding apparatus 5 may include more than one defect sensor 24. Defect sensor 24 may be configured to evaluate each cut web product, or any desired subset, sampling, etc. thereof. For example, in an embodiment, it may be desirable to sample a certain fraction of cut web products, and then, if appropriate, to group the sampled product with those adjacent to it. By way of example only, if the defect sensor 24 detects every third cut web product 20, that sensed product may be treated as representative of those that precede and follow it.

In a further embodiment, cut web products 20 that contain at least one defect or otherwise do not meet satisfactory conditions may be selected to bypass folding mechanism 18, such that the defective cut web products 72 (shown in FIG. 9) are not folded or delivered to second pathway 10. In some embodiments, defective cut web products 72 may be delivered to an alternate pathway or may be subjected to alternate processes, such as testing, destruction, other commercial or other uses, etc.

Figure 9:
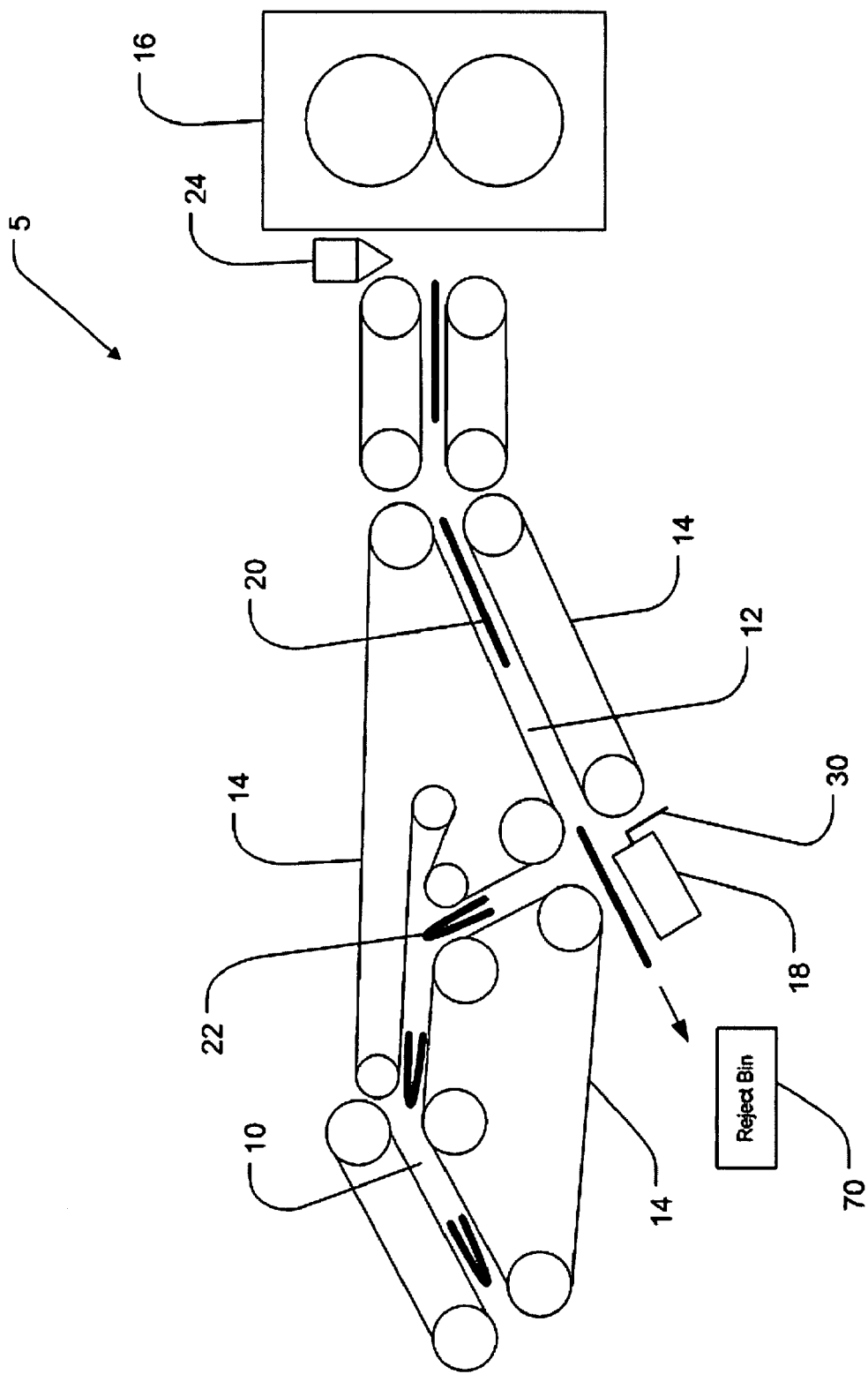
FIG. 9 is a side view of a selective folding apparatus in accordance with another embodiment of the present disclosure.

A further embodiment of selective folding apparatus 5, shown in FIG. 9, includes a location where cut web products 72, which have been determined to contain a defect or are unsatisfactory for any reason, are delivered. In FIG. 9, cut web products 72 that have been determined to contain a defect or are unsatisfactory for any reason are delivered to reject bin 70. In some embodiments, reject bin 70 may comprise a removable bin where defective cut web products 72 are delivered or disposed. In other embodiments reject bin 70 may be an incinerator, a trash compactor, or any other suitable device for disposal of defective cut web products 72. In yet further embodiments, cut web products 72 that have been determined to contain a defect or are unsatisfactory for any reason may be delivered to further paths or subjected to further processes, including but not limited to, testing, destruction, etc.

As illustrated in FIG. 9, in an embodiment, cut web products 20 are delivered, manually or mechanically, to first pathway 12. Cut web products 20, travel along first pathway 12 by means of conveyor system 14. As previously stated, in an embodiment, conveyor system 14 comprises a belt and roller system. In other embodiments, conveyor system 14 may comprise any other suitable conveyor means of causing cut web products 20 to travel along first pathway 12. Cut web products travel along first pathway 12 toward folding mechanism 18.

In an embodiment, folding mechanism 18 may selectively cause cut web products 20 to be folded and may further cause the folded cut web products 22 to be delivered to second pathway 10 or multiple second pathways as described with reference to FIG. 2. In some embodiments, folded cut web products 22 may travel along second pathway 10 by means of conveyor system 14 toward an exit of selective folding apparatus 5, as was described with reference to FIG. 1.

In some embodiments, however, where a cut web product 20 has been determined to contain a defect or is unsatisfactory for any reason, folding mechanism 18 may be caused to be slowed, including substantially slowed, in order to allow defective cut web product 72 to bypass folding mechanism 18. In a further embodiment of selective folding apparatus 5, folding mechanism 18 may be caused to be nearly stopped, substantially stopped, or stopped completely, to allow defective cut web product 72 to bypass folding mechanism 18. Folding mechanism 18 may allow defective cut web product 72 to pass without folding defective cut web product 72. Similarly, folding mechanism 18 may allow defective cut web product 72 to pass without delivering defective cut web product 72 to second pathway 10. In an embodiment, folding mechanism 18 may be slowed, substantially slowed, or stopped, such that the tucker blade or tucker arm does not come into contact with defective cut web product 72. That is, folding mechanism 18 may be slowed, substantially slowed, or stopped, such that the tucker blade or tucker arm is in a position that does not block defective cut web product 72 from bypassing folding mechanism 18.

In a further embodiment, folding mechanism 18 may be accelerated, or substantially accelerated, such that the tucker blades or tucker arm may be allowed to pass through first pathway 12 between consecutive cut web products 20, such that the tucker blades or tucker arm do not contact defective cut web products 72. Subsequent to acceleration, folding mechanism 18 may reduce its speed to substantially the same speed as during prior operation, or another suitable speed, such that the tucker blades or tucker arm may continue to pass through first pathway 12 between consecutive defective cut web products 72, thereby allowing consecutive defective cut web products 72 to bypass folding mechanism 18. That is, folding mechanism 18 may be accelerated or substantially accelerated, and then slowed or substantially slowed, such that the tucker blades or tucker arm are in a position that does not redirect defective cut web products 72 to second pathway 10. That is, folding mechanism 18 may be accelerated or substantially accelerated, and then slowed or substantially slowed, such that the tucker blades or tucker arm are out of phase with cut web products 20 traveling along first pathway 12. In an embodiment, folding mechanism 18 may be accelerated or substantially accelerated, and then slowed or substantially slowed, such that a single defective cut web product 72 is allowed to bypass folding mechanism 18, and then folding mechanism 18 may be phased, by acceleration or deceleration, back in accordance with cut web products 20 traveling along first pathway 12, such that cut web products 20 are once again folded and delivered to second pathway 10. In other embodiments, more than a single consecutive defective cut web product 72 may be allowed to bypass folding mechanism 18 before folding mechanism 18 is phased back in accordance with cut web products 20.

In a further embodiment, folding mechanism 18 may be decelerated, or substantially decelerated, such that the tucker blades or tucker arm may be allowed to pass through first pathway 12 between consecutive cut web products 20, such that the tucker blades or tucker arm do not contact defective cut web products 72. Subsequent to deceleration, folding mechanism 18 may increase its speed to substantially the same speed as during prior operation, or another suitable speed, such that the tucker blades or tucker arm may continue to pass through first pathway 12 between consecutive defective cut web products 72, thereby allowing consecutive defective cut web products 72 to bypass folding mechanism 18. That is, folding mechanism 18 may be decelerated or substantially decelerated, and then accelerated or substantially accelerated, such that the tucker blades or tucker arm are in a position that does not redirect defective cut web products 72 to second pathway 10. That is, folding mechanism 18 may be decelerated or substantially decelerated, and then accelerated or substantially accelerated, such that the tucker blades or tucker arm are out of phase with cut web products 20 traveling along first pathway 12. In an embodiment, folding mechanism 18 may be decelerated or substantially decelerated, and then accelerated or substantially accelerated, such that a single defective cut web product 72 is allowed to bypass folding mechanism 18, and then folding mechanism 18 may be phased, by acceleration or deceleration, back in accordance with cut web products 20 traveling on first pathway 12, such that cut web products 20 are once again folded and delivered to second pathway 10. In other embodiments, more than a single consecutive defective cut web product 72 may be allowed to bypass folding mechanism 18 before folding mechanism 18 is phased back in accordance with cut web products 20.

As stated previously, defective cut web product 72 may bypass folding mechanism 18 and travel toward reject bin 70. In other embodiments, defective cut web product 72 may bypass folding mechanism 18 and travel toward further paths or subjected to further processes, including but not limited to testing, destruction, etc. After defective cut web product 72 bypasses folding mechanism 18, folding mechanism 18 may be accelerated to operating speed or another speed. In an embodiment, folding mechanism 18 may be accelerated to operating speed by the time the next consecutive cut web product 20 immediately following defective cut web product 72 reaches folding mechanism 18. Although the present disclosure has been described with reference to preferred embodiments, persons skilled in the art will recognize that changes may be made in form and detail without departing from the spirit and scope of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for rejecting defective cut web products in a web product producing apparatus comprising:
   advancing a plurality of cut web products along a first path;
   determining whether one or more cut web products are defective;
   rotating a tucker blade to engage web products advancing along the first path to fold the cut web products and deliver the folded cut web products to a second path; and
   slowing the rotation of the tucker blade when it is determined that a cut web product is defective, such that the defective cut web product is not delivered to the second path.

2. The method of claim 1, further comprising the step of stopping the rotation of the tucker blade when it is determined that a cut web product is defective, such that the defective cut web product is not delivered to the second path.

3. The method of claim 2, further comprising providing a drive mechanism for controlling the rotation of the tucker blade, the drive mechanism containing programming to one of slow, substantially slow, and stop the rotation of the tucker blade and to accelerate the rotation of the tucker blade.

4. The method of claim 3, wherein the drive mechanism is a servo motor.

5. The method of claim 4, wherein the servo motor is directly attached to the tucker blade.

6. The method of claim 4, wherein the servo motor is linked to the tucker blade by one of at least one belt drive, at least one gear, and at least one gearbox.

7. A method for rejecting defective cut web products comprising:
   advancing a plurality of individual cut web products along a first path;
   determining whether one or more cut web products contains a defect;
   providing a tucker blade along the first path for delivering the cut web products to a second path, the tucker blade rotating at an operating speed;
   wherein the rotation of the tucker blade is at least one of accelerated, substantially accelerated, decelerated, and substantially decelerated when it is determined that a cut web product contains a defect, such that the defective cut web product is not delivered to the second path, and further wherein the rotation of the tucker blade is one of accelerated and decelerated back to substantially the operating speed and phased with the cut web products by the time the next non-defective cut web product advancing along the first path reaches the tucker blade.

8. The method of claim 7, wherein the cut web products are not folded when the cut web products are delivered to the second path.

9. The method of claim 7, wherein the rotation of the tucker blade is at least one of accelerated, substantially accelerated, decelerated, and substantially decelerated and then correspondingly at least one of decelerated, substantially decelerated, accelerated, and substantially accelerated, such that the rotation of the tucker blade is out of phase with the plurality of individual cut web products traveling along the first path and wherein the cut web products are not delivered to the second path.

10. A method for rejecting defective cut web products comprising:
    advancing a plurality of individual cut web products along a first path;
    determining whether one or more cut web products contains a defect;
    providing a tucker blade having a distal portion and a proximal portion;
    rotating the distal portion of the tucker blade around the proximal portion of the tucker blade to engage the distal portion with web products advancing along the first path to fold the cut web products and deliver the folded cut web products to a second path; and
    slowing the rotation of the distal portion of the tucker blade around the proximal portion such that a defective cut web product is not delivered to the second path.

11. The method of claim 10, further comprising the step of stopping the rotation of the distal portion of the tucker blade such that the defective cut web product is not delivered to the second path.

12. The method of claim 10, further comprising providing a drive mechanism for controlling the rotation of the distal portion of the tucker blade, the drive mechanism including programming to one of slow, substantially slow, and stop the rotation of the tucker blade and to accelerate the rotation of the distal portion of the tucker blade.

13. The method of claim 12, wherein the drive mechanism is a servo motor.

14. The method of claim 13, wherein the servo motor is directly connected with the tucker blade.

15. The method of claim 13, wherein the servo motor is linked to the tucker blade by one of at least one belt drive, at least one gear, and at least one gearbox.

* * * * *